(12) United States Patent
Cho

(10) Patent No.: US 11,476,379 B2
(45) Date of Patent: Oct. 18, 2022

(54) PHOTOSENSITIVE DEVICE, X-RAY DETECTOR AND DISPLAY DEVICE

(71) Applicant: HKC CORPORATION LIMITED, Guangdong (CN)

(72) Inventor: En-tsung Cho, Guangdong (CN)

(73) Assignee: HKC CORPORATION LIMITED, Shenzhen (CN)

( * ) Notice: Subject to any disclaimer, the term of this patent is extended or adjusted under 35 U.S.C. 154(b) by 154 days.

(21) Appl. No.: 17/253,065

(22) PCT Filed: Dec. 27, 2019

(86) PCT No.: PCT/CN2019/129308
§ 371 (c)(1),
(2) Date: Dec. 16, 2020

(87) PCT Pub. No.: WO2020/143484
PCT Pub. Date: Jul. 16, 2020

(65) Prior Publication Data
US 2021/0135036 A1    May 6, 2021

(30) Foreign Application Priority Data
Jan. 11, 2019   (CN) .......................... 201910030104.X

(51) Int. Cl.
*H01L 31/08* (2006.01)
*H01L 27/144* (2006.01)
(Continued)

(52) U.S. Cl.
CPC .......... *H01L 31/085* (2013.01); *H01L 27/144* (2013.01); *H01L 27/14659* (2013.01);
(Continued)

(58) Field of Classification Search
None
See application file for complete search history.

(56) References Cited

U.S. PATENT DOCUMENTS 7,679,158 B2    3/2010   Imai
9,306,098 B2 *  4/2016   Huang ............. H01L 21/02485
(Continued)

FOREIGN PATENT DOCUMENTS

CN     1336785 A     2/2002
CN     101919023 A   12/2010
(Continued)

OTHER PUBLICATIONS

International Search Report dated Mar. 26, 2020; PCT/CN2019/129308.
(Continued)

*Primary Examiner* — Steven M Christopher
(74) *Attorney, Agent, or Firm* — Westbridge IP LLC

(57) ABSTRACT

The present disclosure provides a photosensitive device, including: a photosensitive layer (1) formed by stacking a plurality of fillers, each of the fillers being a uniformly distributed nanopore structure, the nanopore structure being filled with gaseous selenium; a first electrode (2) provided on a light incident side of the photosensitive layer (1); and a second electrode (3) provided on a light exit side of the photosensitive layer (1). The present disclosure further provides an X-ray detector and a display device.

20 Claims, 2 Drawing Sheets

(51) Int. Cl.
  *H01L 27/146* (2006.01)
  *H01L 31/0272* (2006.01)
  *H01L 31/0352* (2006.01)

(52) U.S. Cl.
  CPC ...... *H01L 31/0272* (2013.01); *H01L 31/0352* (2013.01); *H01L 27/14612* (2013.01)

(56) References Cited

U.S. PATENT DOCUMENTS

| | | | |
|---|---|---|---|
| 2001/0008271 A1 | 7/2001 | Ikeda et al. | |
| 2005/0092992 A1 | 5/2005 | Nagata et al. | |
| 2014/0283913 A1* | 9/2014 | Whitelegg | H01L 31/18 136/265 |
| 2015/0007890 A1* | 1/2015 | Xu | H01L 31/035272 136/260 |
| 2015/0063543 A1 | 3/2015 | Lee et al. | |
| 2018/0122713 A1* | 5/2018 | Voss | H01L 31/032 |
| 2018/0122971 A1* | 5/2018 | Fuyuki | H01L 27/14652 |
| 2021/0135036 A1* | 5/2021 | Cho | H01L 31/085 |
| 2022/0037539 A1* | 2/2022 | Cho | H01L 31/1812 |

FOREIGN PATENT DOCUMENTS

| | | |
|---|---|---|
| CN | 104823280 A | 8/2015 |
| CN | 105514029 A | 4/2016 |
| CN | 109860329 A | 6/2019 |
| JP | 2001255376 A | 9/2001 |

OTHER PUBLICATIONS

Written Opinion dated Mar. 26, 2020; PCT/CN2019/129308.
First Chinese Office Action Application No. 201910030104; dated May 6, 2020.

* cited by examiner

PHOTOSENSITIVE DEVICE, X-RAY DETECTOR AND DISPLAY DEVICE

CROSS-REFERENCE TO RELATED APPLICATIONS

This application is the National Stage of International Application No. PCT/CN2019/129308, filed on Dec. 27, 2019, which claims priority to Chinese Application No. 201910030104.X, filed on Jan. 11, 2019, entitled "PHOTOSENSITIVE DEVICE, X-RAY DETECTOR AND DISPLAY DEVICE", the entire disclosure of which is incorporated herein by reference.

TECHNICAL FIELD

The present disclosure relates to the technical field of detectors, in particular to a photosensitive device, an X-ray detector and a display device.

BACKGROUND

The statements here only provide background information related to the present disclosure, and do not necessarily constitute related art.

X-ray detectors are widely used in medical instruments, such as chest X-ray imaging using X-rays. In the exemplary technology, the photoelectric conversion of the X-ray detector is mainly completed by the amorphous silicon photosensitive layer. X-rays are converted into visible light by the scintillator (currently mainly CsI), and then the visible light is converted into electrical signals by the amorphous silicon photosensitive layer, and the electrical signals are output by the signal reading device (Thin film transistor, TFT for short). Since the structure of amorphous silicon is not stable enough and the light conversion efficiency is low, causing the amorphous silicon photosensitive layer absorbs a wide range of light waves and is not sensitive to light conversion, which directly affects the photoelectric conversion efficiency of the X-ray detector.

SUMMARY

The main objective of the present disclosure is to provide a photosensitive device, an X-ray detector and a display device, which aims to improve the light absorption efficiency and light conversion efficiency of the X-ray detector.

In order to achieve the above objective, the present disclosure provides a photosensitive device, including:

a photosensitive layer formed by stacking a plurality of fillers, each of the fillers being a uniformly distributed nanopore structure, the nanopore structure being filled with gaseous selenium;

a first electrode provided on a light incident side of the photosensitive layer; and a second electrode provided on a light exit side of the photosensitive layer.

In an embodiment, a pore diameter of the nanopore structure is 2 nm to 10 nm.

In an embodiment, the gaseous selenium is filled into the nanopore structure in a pulsed manner.

In an embodiment, each of the fillers is formed of $Si_xO_y$.

In an embodiment, each of the fillers is a strip filler.

In an embodiment, the first electrode is electrically connected to the photosensitive layer, and the second electrode is electrically connected to a signal reading element.

In an embodiment, the first electrode is a transparent electrode, and the second electrode is a metal electrode.

In an embodiment, the second electrode has an in-line structure.

In an embodiment, the second electrode has a T-shaped structure.

In an embodiment, the photosensitive device is a direct photosensitive detector.

In an embodiment, an X-ray detector includes a substrate and a photosensitive device provided on a light incident side of the X-ray detector to sense an optical intensity of X-rays and convert the optical intensity into an electrical signal;

the X-ray detector further includes:

a signal reading element provided on the substrate and electrically connected to the photosensitive device to receive and read the electric signal converted by the photosensitive device;

the photosensitive device including:

a photosensitive layer formed by stacking a plurality of fillers, each of the fillers being a uniformly distributed nanopore structure, the nanopore structure being filled with gaseous selenium;

a first electrode provided on a light incident side of the photosensitive layer; and a second electrode provided on a light exit side of the photosensitive layer.

In an embodiment, a pore diameter of the nanopore structure is 2 nm to 10 nm.

In an embodiment, each of the fillers is formed of $Si_xO_y$.

In an embodiment, the first electrode is a transparent electrode, and the second electrode is a metal electrode.

In an embodiment, the X-ray detector further includes a protective layer filling a gap between the signal reading element and the photosensitive device to isolate the signal reading element from an external environment.

In an embodiment, a thickness of the protective layer is 500 nm to 2000 nm.

In an embodiment, the second electrode penetrates the protective layer and is electrically connected to a drain of the signal reading element.

In an embodiment, the second electrode is electrically connected to a drain of the signal reading element through a wire.

In an embodiment, a display device includes an X-ray detector, the an X-ray detector including a substrate and a photosensitive device provided on a light incident side of the X-ray detector to sense an optical intensity of X-rays and convert the optical intensity into an electrical signal;

the X-ray detector further includes:

a signal reading element provided on the substrate and electrically connected to the photosensitive device to receive and read the electric signal converted by the photosensitive device;

the photosensitive device including:

a photosensitive layer formed by stacking a plurality of fillers, each of the fillers being a uniformly distributed nanopore structure, the nanopore structure being filled with gaseous selenium;

a first electrode provided on a light incident side of the photosensitive layer; and a second electrode provided on a light exit side of the photosensitive layer.

In an embodiment, the display device further includes an imaging device electrically connected to the signal reading element.

The present disclosure provides a photosensitive device, an X-ray detector and a display device. The photosensitive device includes a photosensitive layer formed by stacking a plurality of fillers, each of the fillers being a uniformly distributed nanopore structure, the nanopore structure being filled with gaseous selenium; a first electrode provided on a light incident side of the photosensitive layer; and a second electrode provided on a light exit side of the photosensitive layer. In some embodiments of the present disclosure, the photosensitive layer is formed by stacking a plurality of fillers, the filler is a uniformly distributed nanopore structure, and the nanopore structure is filled with gaseous selenium, to increase the contact area of light, and increase the light sensitivity of the photosensitive layer, thereby improving the light absorption efficiency of the photosensitive layer, and improving the light conversion efficiency of the photosensitive layer.

BRIEF DESCRIPTION OF THE DRAWINGS

In order to more clearly illustrate the embodiments of the present disclosure, drawings used in the embodiments will be briefly described below. Obviously, the drawings in the following description are only some embodiments of the present disclosure. It will be apparent to those skilled in the art that other figures can be obtained according to the structures shown in the drawings without creative work.

The realization of the objective, functional characteristics and advantages of the present disclosure are further described with reference to the accompanying drawings.

DETAILED DESCRIPTION OF THE EMBODIMENTS

The technical solutions of the embodiments of the present disclosure will be described in more detail below with reference to the accompanying drawings. It is obvious that the embodiments to be described are only some rather than all of the embodiments of the present disclosure. All other embodiments obtained by persons skilled in the art based on the embodiments of the present disclosure without creative efforts shall fall within the scope of the present disclosure.

It should be noted that, if there are directional indications (such as up, down, left, right, front, rear . . . ) in the embodiments of the present disclosure, the directional indication is only used to explain the relative positional relationship, movement, etc. between the various components in a specific posture (as shown in the figure). If the specific posture changes, the directional indication will change accordingly.

In addition, the descriptions associated with, e.g., "first" and "second," in the present disclosure are merely for descriptive purposes, and cannot be understood as indicating or suggesting relative importance or impliedly indicating the number of the indicated technical feature. Therefore, the feature associated with "first" or "second" can expressly or impliedly include at least one such feature. Besides, the technical solutions between the various embodiments can be combined with each other, but they must be based on the realization of those of ordinary skill in the art. When the combination of technical solutions is contradictory or cannot be achieved, it should be considered that such a combination of technical solutions does not exist, nor is it within the scope of the present disclosure.

Figure 1:
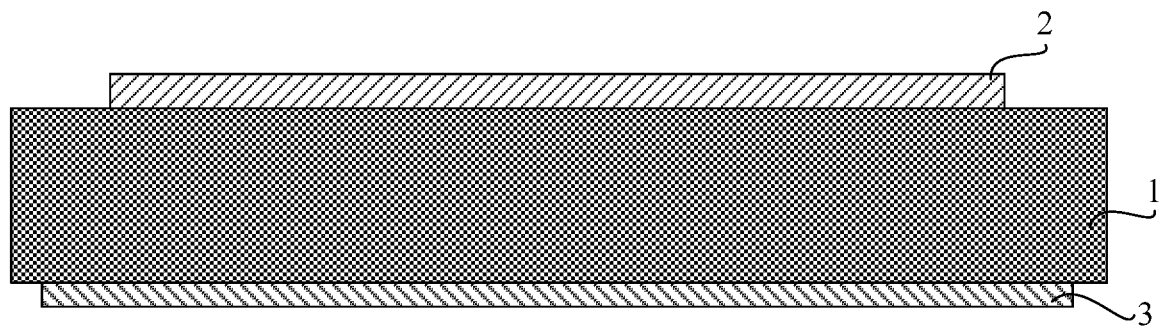
FIG. 1 is a schematic structural diagram of a photosensitive device according to an embodiment of the present disclosure.
Figure 2:
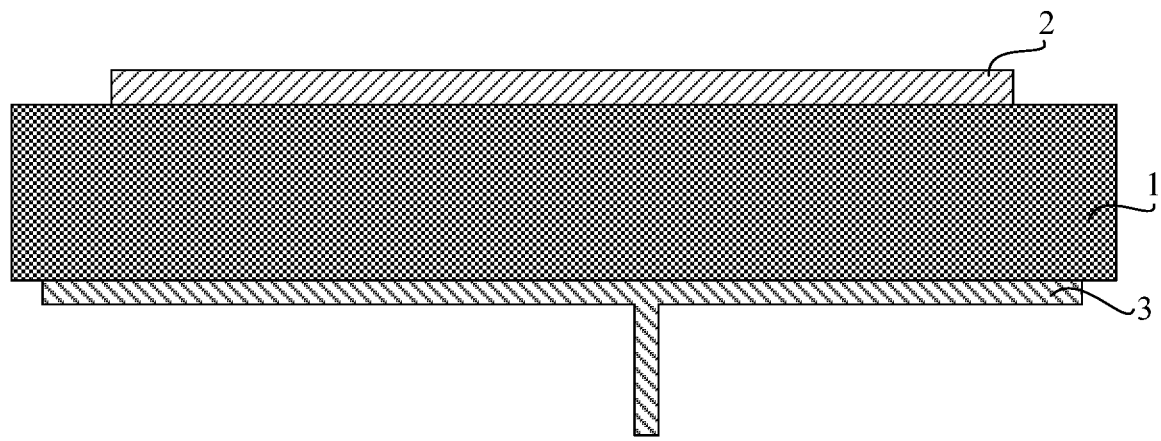
FIG. 2 is a schematic structural diagram of the photosensitive device according to another embodiment of the present disclosure.

As shown in FIGS. 1 and 2, the present disclosure provides a photosensitive device.

As shown in FIGS. 1 and 2, the photosensitive device includes a photosensitive layer 1, a first electrode 2 and a second electrode 3. The photosensitive layer 1 is configured to sense an intensity of light, and convert an optical signal of the light into an electrical signal, thereby transmitting the electrical signal to the signal reading element. In an embodiment, the photosensitive layer 1 is in direct contact with light, that is, the light directly irradiates the photosensitive layer 1, that is, the photosensitive device of the present disclosure is a direct photosensitive detector. Specifically, the light received by the photosensitive layer 1 is X-rays. Through the photoelectric conversion function, the optical signal of X-rays is converted into the electrical signal, which is transmitted to the signal reading element through the second electrode 3 for the signal reading element to read, that is, the photosensitive device of the present disclosure is a direct X-ray detector.

In an embodiment, the first electrode 2 and the second electrode 3 are provided on opposite sides of the photosensitive layer 1, that is, the first electrode 2 is provided on the light incident side of the photosensitive layer 1, and the second electrode 3 is provided on the light exit side of the photosensitive layer 1. In this embodiment, the definition of the light incident side and the light exit side is set for the X-rays emitted by the external X-ray generator. When the position of the X-ray generator changes, that is, the positions of the light incident side and the light exit side of the photosensitive layer 1 also change, which will not be repeated here. The second electrode 3 is electrically connected to the above-mentioned signal reading element, so as to convert the optical signal received by the photosensitive layer 1 into the electrical signal and then directly transmit the electrical signal to the signal reading element through the second electrode 3. There is no need to convert external X-rays into visible light and then transmit them to the signal reading element, thereby improving the efficiency of light absorption.

In an embodiment, the photosensitive layer 1 is formed by stacking a plurality of fillers. Each filler has a uniformly distributed nanopore structure, and the nanopore structure is filled with gaseous selenium (Se). Specifically, each filler is a strip filler with a uniformly distributed nanopore structure inside. The nanopore structure is similar to a honeycomb pore. In this embodiment, gaseous selenium is filled into the nanoporous structure to increase a contact area of the photosensitive layer 1. That is, when light is irradiated on the photosensitive layer 1, the light directly acts on the filler and acts on the gaseous selenium of the nanoporous structure. Therefore, the contact area of light is increased to increase the light sensitivity of the photosensitive layer 1 and the light absorption efficiency of the photosensitive layer 1, that is, the light conversion efficiency of the photosensitive layer 1 is indirectly improved.

In an embodiment, a plurality of fillers are stacked in the photosensitive layer 1 and can make the photosensitive layer 1 in a saturated state, such that the light absorption efficiency is higher. In this embodiment, the number of fillers can be set according to the preparation of the photosensitive layer 1, which is not limited here.

In an embodiment, the gaseous selenium may be filled into the nanopore structure in a pulsed manner. Of course, in other embodiments, the gaseous selenium may be filled into the nanopore structure in other ways, which is not limited here.

In an embodiment, the first electrode 2 is electrically connected to the photosensitive layer 1, and the second electrode 3 is electrically connected to the signal reading element. When a voltage is applied across the first electrode 2 and the second electrode 3, the light is incident on the photosensitive layer 1 from the first electrode 2. After the photosensitive layer 1 senses the light, it detects an intensity of the light and converts an optical signal of the light into an electrical signal. The electrical signal in this embodiment is a current signal, that is, when the optical intensity is strong, the current signal is large; when the optical intensity is weak, the current signal is small. The photosensitive layer 1 transmits the converted electrical signal to the signal reading element through the second electrode 3.

In an embodiment, the photosensitive layer 1 may be in direct contact with light, which reduces the loss of light and improves the utilization of light.

In some embodiments of the present disclosure, the photosensitive layer 1 is formed by stacking a plurality of fillers. Each of the fillers is a uniformly distributed nanopore structure, and the nanopore structure is filled with gaseous selenium. The first electrode 2 is provided on a light incident side of the photosensitive layer 1. The second electrode 3 is provided on a light exit side of the photosensitive layer 1. In some embodiments of the present disclosure, the photosensitive device includes a photosensitive layer 1 formed by stacking a plurality of fillers, each filler is a uniformly distributed nanopore structure, and the nanopore structure is filled with gaseous selenium, thus to increase a contact area of light, and increase the light sensitivity of the photosensitive layer 1, thereby improving the light absorption efficiency of the photosensitive layer 1, and improving the light conversion efficiency of the photosensitive layer 1.

In an embodiment, a pore diameter of the nanopore structure is 2 nm to 10 nm.

Further, the pore diameter of the nanopore structure is 6 nm, such that there may be more gaseous selenium contained in the nanopore structure, and a space of the nanopore structure reaches a saturated state, thereby improving a utilization rate of the nanopore structure and light absorption efficiency. Of course, in other embodiments, the pore diameter of the nanopore structure is any value (excluding 6 nm) from 2 nm to 10 nm, which is not limited here.

In an embodiment, the filler is formed of $Si_xO_y$ (silicon oxide), that is, the filler is a silicon oxide material.

Specially, the silicon oxide crystals are dissolved in the alcohol solution, so that the alcohol solution contains surfactants to induce silicon oxide. The evaporation of alcohol increases a concentration of surfactant. When the concentration of surfactant approaches 10%, the silica oxide begins to form a porous structure. When the concentration reaches 35%, the pore structure of silicon oxide is relatively uniform, and they are closely arranged into a honeycomb shape. This state continues until the concentration of surfactant exceeds 70%. When the concentration exceeds 70%, silicon oxide forms a layered liquid crystal, and it is not convenient for the gaseous selenium to fill the silicon oxide filler. That is, when the silicon oxide crystals are dissolved in the alcohol solution and the concentration of the surfactant in the alcohol solution is 35% to 70%, the gaseous selenium is convenient to be filled into the filler.

In an embodiment, the concentration of the surfactant may control a size of the nanopore, and the pore diameter of the nanopore is between 2 nm and 10 nm. Of course, the type of surfactant may also control the size of nanopores. For example, when the surfactant is P123, the pore diameter of the nanopore is in the range of 5 nm to 10 nm. When the surfactant is CTAB, the pore diameter of the nanopore is in the range of 2 nm to 4.5 nm. When the surfactant is F127, the pore diameter of the nanopore is in the range of 2.5 nm to 4.5 nm. By controlling the pore diameter of the nanopore, the filler can be controlled to absorb light with a specific wavelength, so that the filler can stably absorb light with a wavelength in a specific range. Therefore, the gaseous selenium in the nanopore has a more sensitive response to light and a higher photoelectric conversion efficiency than amorphous silicon. It is understandable that the types of surfactants are not limited to the above three types.

In an embodiment, in order to make the light absorption efficiency of the photosensitive layer 1 higher, the first electrode 2 is a transparent electrode, that is, light can directly pass through the first electrode 2. It should be understood that light can be directly transmitted through the first electrode 2 and irradiate the photosensitive layer 1, that is, the transparent electrode also has high light transmittance, such that it can transmit light, thereby reducing light loss and improving light utilization.

In an embodiment, since the second electrode 3 is electrically connected to the aforementioned signal reading element 5, that is, the second electrode 3 is a metal electrode. While the electrical signal can be conducted, the signal reading element 5 can be covered by utilizing the opacity of metal to prevent light from entering the signal reading element, thereby causing inaccuracy in reading the signal. Specifically, the material of the metal electrode may be a metal material including copper, nickel, etc., which is not limited here.

In an embodiment, the second electrode 3 may have an in-line structure (as shown in FIG. 1), or a T-shaped structure (as shown in FIG. 2). Of course, in order to cooperate with the signal reading element, the second electrode 3 may also have other structures, which are not limited in the present disclosure.

In some embodiments of the present disclosure, the photosensitive layer 1 is formed by stacking a plurality of fillers. Each of the fillers is a uniformly distributed nanopore structure, and the nanopore structure is filled with gaseous selenium. The first electrode 2 is provided on a light incident side of the photosensitive layer 1. The second electrode 3 is provided on a light exit side of the photosensitive layer 1. In the present disclosure, the photosensitive device includes a photosensitive layer 1 formed by stacking a plurality of fillers, the filler is a uniformly distributed nanopore structure, and the nanopore structure is filled with gaseous selenium, to increase a contact area of light, and increase the light sensitivity of the photosensitive layer 1, thereby improving the light absorption efficiency of the photosensitive layer 1, and improving the light conversion efficiency of the photosensitive layer 1.

Figure 3:
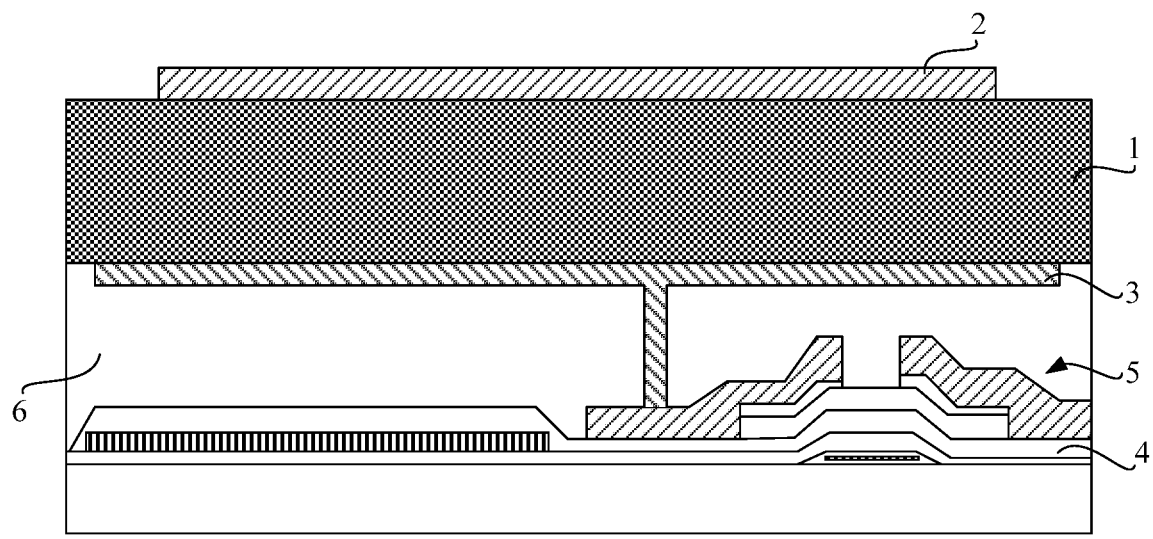
FIG. 3 is a schematic structural diagram of an X-ray detector according to an embodiment of the present disclosure.

Based on the above embodiment, another embodiment of the present disclosure further provides an X-ray detector. As shown in FIG. 3, the X-ray detector includes a substrate 4 and the photosensitive device in the above-mentioned embodiment. The photosensitive device is provided on the light incident side of the X-ray detector to sense an optical intensity of X-rays and convert it into an electrical signal. In this embodiment, the definition of the light incident side is set for the X-rays emitted by the external X-ray generator. When the position of the X-ray generator changes, that is, the position of the light incident side of the X-ray detector also changes, which will not be repeated here.

In an embodiment, as shown in FIGS. 1 and 2, the photosensitive device includes a photosensitive layer 1, a first electrode 2 and a second electrode 3. The photosensitive layer 1 is formed by stacking a plurality of fillers, each filler is a uniformly distributed nanopore structure, and the nanopore structure is filled with gaseous selenium (Se). The first electrode 2 is provided on the light incident side of the photosensitive layer 1, and the second electrode 3 is provided on the light exit side of the photosensitive layer 1, to increase a contact area of light, and increase the light sensitivity of the photosensitive layer 1, thereby improving the light absorption efficiency of the photosensitive layer 1, and improving the light conversion efficiency of the photosensitive layer 1.

Further, a pore diameter of the nanopore structure is 2 nm to 10 nm. In the present disclosure, the pore diameter of the nanopore structure can be 6 nm, such that there may be more gaseous selenium contained in the nanopore structure, and a space of the nanopore structure reaches a saturated state, thereby improving a utilization rate of the nanopore structure and light absorption efficiency. Of course, in other embodiments, the pore diameter of the nanopore structure is any value (excluding 6 nm) from 2 nm to 10 nm, which is not limited here.

Further, the filler is formed of $Si_xO_y$ (silicon oxide), that is, the filler is a silicon oxide material.

Specially, the silicon oxide crystals are dissolved in the alcohol solution, so that the alcohol solution contains surfactants to induce silicon oxide. The evaporation of alcohol increases the concentration of surfactant. When the concentration of surfactant approaches 10%, silica begins to form a porous structure. When the concentration reaches 35%, the pore structure of silicon oxide is relatively uniform, and they are closely arranged into a honeycomb shape. This state continues until the surfactant concentration exceeds 70%. When the concentration exceeds 70%, silicon oxide forms a layered liquid crystal, and gaseous selenium is not convenient to fill the silicon oxide filler. That is, when the silicon oxide crystals are dissolved in the alcohol solution and the concentration of the surfactant in the alcohol solution is 35% to 70%, the gaseous selenium is convenient to be filled into the filler.

Further, in order to make the light absorption efficiency of the photosensitive layer 1 higher, the first electrode 2 is a transparent electrode, that is, light can directly pass through the first electrode 2. It should be understood that light can be directly transmitted through the first electrode 2 and irradiate the photosensitive layer 1, that is, the transparent electrode also has high light transmittance, such that it can transmit light, thereby reducing light loss and improving light utilization.

Further, since the second electrode 3 is electrically connected to the aforementioned signal reading element 5, that is, the second electrode 3 is a metal electrode. While the electrical signal can be conducted, the signal reading element 5 can be covered by utilizing the opacity of metal to prevent light from entering the signal reading element, thereby causing inaccuracy in reading the signal. Specifically, the material of the metal electrode may be a metal material including copper, nickel, etc., which is not limited here.

In an embodiment, the X-ray detector also includes a signal reading element 5 provided on the substrate 4 and is electrically connected to the photosensitive device to receive and read the electrical signal converted by the photosensitive device. Specifically, the signal reading element 5 may be a Thin Film Transistor (TFT) structure, and is configured to read the electrical signal of the photosensitive device, and the electrical signal is a current signal.

In an embodiment, the substrate 4 may be a glass substrate 4, a silicon wafer, a polyimide PI plastic substrate 4, etc., which are not limited herein.

In an embodiment, an X-ray generator (not shown) is also provided on the X-ray detector, which is configured to emit X-rays. The X-ray detector is provided on the light incident side of the X-ray generator, that is, the photosensitive layer 1 of the photosensitive device is provided on the light incident side of the X-ray detector. Specially, the photosensitive layer 1 is formed by stacking a plurality of fillers, the filler is a uniformly distributed nanopore structure, and the nanopore structure is filled with gaseous selenium, configured to convent an optical signal of X-rays into an electrical signal and transmit the electrical signal to the signal reading element 5.

Figure 4:
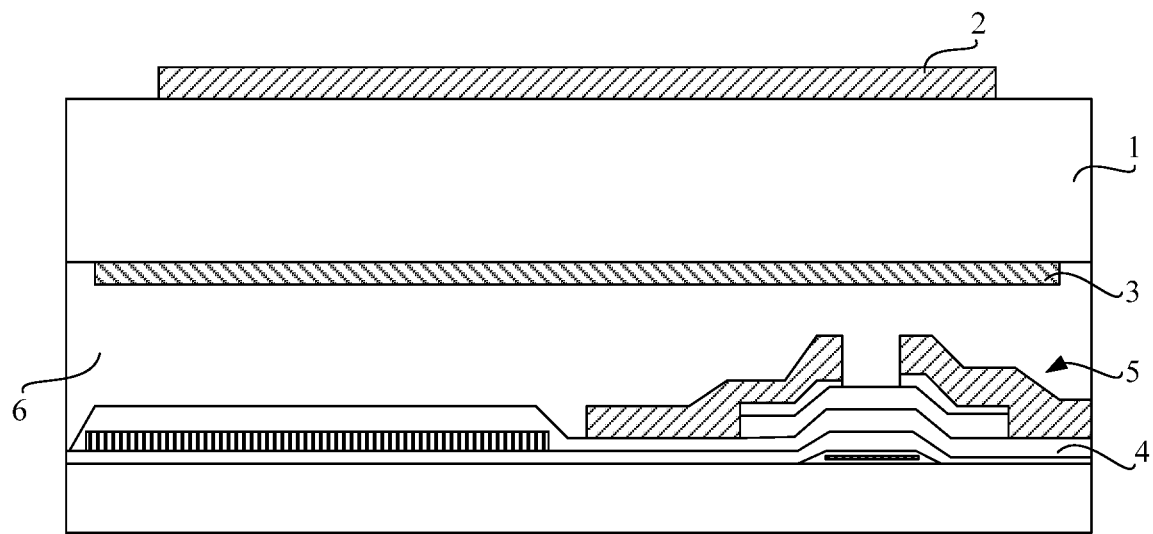
FIG. 4 is a schematic structural diagram of the X-ray detector according to another embodiment of the present disclosure.

In an embodiment, a drain of the signal reading element 5 is provided on the substrate 4 and is electrically connected to the second electrode 3 of the photosensitive device to conduct electrical signals. Of course, as shown in FIG. 3, the second electrode 3 is a T-shaped electrode, that is, the second electrode 3 penetrates the protective layer 6 and is electrically connected to the drain of the signal reading element 5, so that the conduction of electrical signals is more efficient and faster. In another embodiment, as shown in FIG. 4, the second electrode 3 is an in-line electrode, the second electrode 3 is electrically connected to the drain of the signal reading element 5 through a wire, which is not limited in the present disclosure.

In a specific embodiment, the X-ray detector further includes a protective layer 6 that fills the gap between the signal reading element 5 and the photosensitive device to isolate the signal reading element 5 from the external environment.

In an embodiment, in order to be able to support the photosensitive device, a thickness of the protective layer 6 is 500 nm to 2000 nm, which can make the structure of the entire X-ray detector more stable and ensure the flatness of the X-ray detector.

In technical solutions of the present disclosure, the photosensitive device includes the photosensitive layer 1 formed by stacking a plurality of fillers, each filler is a uniformly distributed nanopore structure, and the nanopore structure is filled with gaseous selenium, to increase a contact area of light, and increase the light sensitivity of the photosensitive layer 1, thereby improving the light absorption efficiency of the photosensitive layer 1, and improving the light conversion efficiency of the photosensitive layer 1.

Based on all the foregoing embodiments, as shown in FIGS. 1 to 4, an embodiment of the present disclosure further provides a display device. The display device includes the aforementioned X-ray detector and an imaging device (not shown), the X-ray detector is electrically connected to the imaging device. The electric signal generated by the X-ray detector due to the photoelectric effect forms an image through the imaging device.

In an embodiment, as shown in FIGS. 1 and 2, the photosensitive device includes a photosensitive layer 1, a first electrode 2 and a second electrode 3. The photosensitive layer 1 is formed by stacking a plurality of fillers, each filler is a uniformly distributed nanopore structure, and the nanopore structure is filled with gaseous selenium (Se). The first electrode 2 is provided on the light incident side of the photosensitive layer 1, and the second electrode 3 is provided on the light exit side of the photosensitive layer 1.

In an embodiment, as shown in FIGS. 3 to 4, the X-ray detector includes a substrate 4 and the photosensitive device in the above embodiment. The photosensitive device is provided on the light incident side of the X-ray detector to sense the optical intensity of the X-ray and convert the optical intensity into an electrical signal.

Further, the X-ray detector includes a signal reading element 5 provided on the substrate 4 and is electrically connected to the photosensitive device to receive and read the electrical signal converted by the photosensitive device. Specifically, the signal reading element 5 may be a Thin Film Transistor (TFT) structure, and is configured to read the electrical signal of the photosensitive device, and the electrical signal is a current signal.

In an embodiment, since the photosensitive device with the photoelectric conversion function in the X-ray detector has sensitive and efficient photoelectric conversion performance, under the same imaging effect, the irradiation intensity or irradiation time of X-ray can be reduced, and the impact on the patient can be reduced.

The technical solution of the present disclosure adopts the above-mentioned X-ray detector. A plurality of fillers are stacked in the photosensitive layer 1 of the photosensitive device in the X-ray detector. Each filler is a uniformly distributed nanopore structure, and the nanopore structure is filled with gaseous selenium, to increase a contact area of light, and increase the light sensitivity of the photosensitive layer 1, thereby improving the light absorption efficiency of the photosensitive layer 1, and improving the light conversion efficiency of the photosensitive layer 1.

The above are only optional embodiments of the present disclosure, and do not limit the scope of the present disclosure. Under the inventive concept of the present disclosure, any equivalent structural transformations made using the contents of the description and drawings of the present disclosure, or direct/indirect application in other related technical fields are included in the scope of the present disclosure.

What is claimed is:

1. A photosensitive device, comprising:
   a photosensitive layer formed by stacking a plurality of fillers, each of the fillers being a uniformly distributed nanopore structure, the nanopore structure being filled with gaseous selenium;
   a first electrode provided on a light incident side of the photosensitive layer; and
   a second electrode provided on a light exit side of the photosensitive layer.

2. The photosensitive device of claim 1, wherein a pore diameter of the nanopore structure is 2 nm to 10 nm.

3. The photosensitive device of claim 1, wherein the gaseous selenium is filled into the nanopore structure in a pulsed manner.

4. The photosensitive device of claim 1, wherein each of the fillers is formed of $Si_xO_y$.

5. The photosensitive device of claim 4, wherein each of the fillers is a strip filler.

6. The photosensitive device of claim 1, wherein the first electrode is electrically connected to the photosensitive layer, and the second electrode is electrically connected to a signal reading element.

7. The photosensitive device of claim 6, wherein the first electrode is a transparent electrode, and the second electrode is a metal electrode.

8. The photosensitive device of claim 1, wherein the second electrode has an in-line structure.

9. The photosensitive device of claim 1, wherein the second electrode has a T-shaped structure.

10. The photosensitive device of claim 1, wherein the photosensitive device is a direct photosensitive detector.

11. An X-ray detector, comprising:
    a substrate;
    a photosensitive device provided on a light incident side of the X-ray detector to sense an optical intensity of X-rays and convert the optical intensity into an electrical signal, the photosensitive device comprising:
      a photosensitive layer formed by stacking a plurality of fillers, each of the fillers being a uniformly distributed nanopore structure, the nanopore structure being filled with gaseous selenium;
      a first electrode provided on a light incident side of the photosensitive layer;
      a second electrode provided on a light exit side of the photosensitive layer; and
    a signal reading element provided on the substrate and electrically connected to the photosensitive device to receive and read the electric signal converted by the photosensitive device.

12. The X-ray detector of claim 11, wherein a pore diameter of the nanopore structure is 2 nm to 10 nm.

13. The X-ray detector of claim 11, wherein each of the fillers is formed of $Si_xO_y$.

14. The X-ray detector of claim 11, wherein the first electrode is a transparent electrode, and the second electrode is a metal electrode.

15. The X-ray detector of claim 11, wherein the X-ray detector further comprises a protective layer filling a gap between the signal reading element and the photosensitive device to isolate the signal reading element from an external environment.

16. The X-ray detector of claim 15, wherein a thickness of the protective layer is 500 nm to 2000 nm.

17. The X-ray detector of claim 16, wherein the second electrode penetrates the protective layer and is electrically connected to a drain of the signal reading element.

18. The X-ray detector of claim 16, wherein the second electrode is electrically connected to a drain of the signal reading element through a wire.

19. A display device, comprising:
    an X-ray detector, comprising:
      a substrate;
      a photosensitive device provided on a light incident side of the X-ray detector to sense an optical intensity of X-rays and convert the optical intensity into an electrical signal, the photosensitive device comprising:
        a photosensitive layer formed by stacking a plurality of fillers, each of the fillers being a uniformly distributed nanopore structure, the nanopore structure being filled with gaseous selenium;
        a first electrode provided on a light incident side of the photosensitive layer;
        a second electrode provided on a light exit side of the photosensitive layer; and
      a signal reading element provided on the substrate and electrically connected to the photosensitive device to receive and read the electric signal converted by the photosensitive device.

20. The display device of claim 19, wherein the display device further comprises an imaging device electrically connected to the signal reading element.

* * * * *